(12) United States Patent
Potenza et al.

(10) Patent No.: US 10,403,410 B2
(45) Date of Patent: Sep. 3, 2019

(54) SOURCE WIRE ASSEMBLY FOR RADIOGRAPHIC APPLICATIONS

(71) Applicant: ILLINOIS TOOL WORKS INC., Glenview, IL (US)

(72) Inventors: Matthew A. Potenza, Sterling, MA (US); John H. Crosby, Jr., Concord, MA (US); Steven J. Grenier, Arlington, MA (US)

(73) Assignee: QSA GLOBAL, INC., Burlington, MA (US)

( * ) Notice: Subject to any disclaimer, the term of this patent is extended or adjusted under 35 U.S.C. 154(b) by 51 days.

(21) Appl. No.: 15/742,978

(22) PCT Filed: May 11, 2016

(86) PCT No.: PCT/US2016/031736
§ 371 (c)(1),
(2) Date: Jan. 9, 2018

(87) PCT Pub. No.: WO2017/019148
PCT Pub. Date: Feb. 2, 2017

(65) Prior Publication Data
US 2018/0226164 A1 Aug. 9, 2018

Related U.S. Application Data

(60) Provisional application No. 62/197,873, filed on Jul. 28, 2015, provisional application No. 62/268,720, filed on Dec. 17, 2015.

(51) Int. Cl.
*G21F 5/015* (2006.01)
*A61B 6/10* (2006.01)
(Continued)

(52) U.S. Cl.
CPC .............. *G21F 5/015* (2013.01); *A61B 6/107* (2013.01); *A61B 6/4429* (2013.01); *F16C 1/14* (2013.01);
(Continued)

(58) Field of Classification Search
CPC ..... G21F 5/015; G06F 1/1683; H05K 9/0018; H05K 9/0098
(Continued)

(56) References Cited

U.S. PATENT DOCUMENTS 5,460,592 A * 10/1995 Langton ............... A61N 5/1027
600/7
6,166,388 A 12/2000 Weir et al.
(Continued)

FOREIGN PATENT DOCUMENTS

GB 2061080 5/1981

OTHER PUBLICATIONS

International Search Report issue in PCT/US2016/031736 dated Dec. 21, 2016.

*Primary Examiner* — Jason L McCormack
(74) *Attorney, Agent, or Firm* — McCarter & English, LLP

(57) ABSTRACT

The present disclosure relates to a source wire assembly for radiographic applications, particularly for guiding a gamma ray source through a tubular path, such as with a radiographic projector. The source wire assembly includes a core of flexible metal cable, such as, but not limited to, aircraft cable, which may include wires and/or strands which are woven, twisted, helix wound or braided. A distal end of the source wire assembly is securely engaged to a Radioactive source capsule assembly while a proximal end of the source wire assembly is securely engaged to a connector housing for connection to driving equipment, such as, but not limited (Continued)

to, a push-pull operation associated with a radiographic projector, which may include source wire locking and safety mechanisms.

16 Claims, 2 Drawing Sheets

(51) Int. Cl.
  *A61B 6/00* (2006.01)
  *G21F 3/00* (2006.01)
  *F16C 1/26* (2006.01)
  *F16C 1/14* (2006.01)
  *G21F 1/08* (2006.01)

(52) U.S. Cl.
  CPC .................. *F16C 1/26* (2013.01); *G21F 1/08* (2013.01); *G21F 3/00* (2013.01); *F16C 2316/10* (2013.01)

(58) Field of Classification Search
  USPC ...................................................... 250/496.1
  See application file for complete search history.

(56) References Cited

U.S. PATENT DOCUMENTS

| | | |
|---|---|---|
| 6,481,914 B1 | 11/2002 | Grenier et al. |
| 6,569,076 B1* | 5/2003 | Larsen ................ A61N 5/1002 600/3 |
| 6,616,617 B1 | 9/2003 | Ferrera et al. |
| 6,627,908 B1 | 9/2003 | Han et al. |
| 2003/0181782 A1* | 9/2003 | McDaniel ............ A61N 5/1002 600/3 |
| 2006/0076520 A1* | 4/2006 | Drobnik ................... A61L 2/07 250/506.1 |

* cited by examiner

SOURCE WIRE ASSEMBLY FOR RADIOGRAPHIC APPLICATIONS

This application is National Phase application of PCT International Application PCT/US2016/031736, filed on May 11, 2016, which claims priority under 35 U.S.C. 119(e) of U.S. provisional application Ser. No. 62/197,873, filed on Jul. 28, 2015, and U.S. provisional application Ser. No. 62/268,720, filed on Dec. 17, 2015, the contents of both of which are hereby incorporated by reference in their entirety and for all purposes.

BACKGROUND OF THE DISCLOSURE

Field of the Disclosure

The present disclosure relates to a source wire assembly for radiographic applications, particularly for guiding a gamma ray source through a tubular path, such as with a radiographic projector. The source wire assembly includes a core of flexible metal cable, such as, but not limited to, aircraft cable, which may include wires and/or strands which are woven, helix wound, twisted or braided.

Description of the Prior Art

In the prior art, it is known to drive a gamma or other radiographic source though a tubular path in order to produce radiographic scans with respect to the integrity of a structure, such as a pipe or similar construction. This may be done in connection with a radiographic projector or similar device. Representative prior art includes U.S. Published Patent Application 2011/0309272 entitled "Radiographic Projector", published on Dec. 22, 2011 on behalf of Cole; U.S. Pat. No. 6,627,908 entitled "Radiation Source Assembly and Connector Press Used in Producing Such Assemblies", issued on Sep. 30, 2003 to Han et al.; U.S. Pat. No. 6,481,914 entitled "Radiographic Source Connector with Improved Coupling Mechanism", issued on Nov. 19, 2002 to Grenier et al.; and U.S. Pat. No. 4,827,493 entitled "Radiographic Source", issued on May 2, 1989 to Parsons et al.

Typically, it is desired that a source wire assembly be somewhat stiff or rigid, but with flexibility to accommodate curvature within the tube path and elasticity so that the source wire assembly is not permanently deformed by the curvature within the path.

OBJECTS AND SUMMARY OF THE DISCLOSURE

It is therefore an object of the present disclosure to provide a source wire assembly which is stiff or rigid, but having sufficient flexibility to accommodate curvature within the tube path of a radiological projector (or similar equipment) and with sufficient elasticity to avoid permanent deformation within the curved path.

This and other objects are attained by the present disclosure of a source wire assembly which includes a core of flexible metal cable, such as, but not limited to, aircraft cable, which may include strands which are woven, helix wound, twisted, braided, or otherwise intertwined, the strands further including a plurality of metallic wires which may be woven, helix wound, twisted, braided or otherwise intertwined. This flexibility of the core provides the desired elasticity and eliminates or reduces any permanent deformation of the source wire assembly when driven through curved paths.

BRIEF DESCRIPTION OF THE DRAWINGS

Further objects and advantages of the disclosure will become apparent from the following description and from the accompanying drawings, wherein.

DETAILED DESCRIPTION OF THE PREFERRED EMBODIMENT

Figure 1:
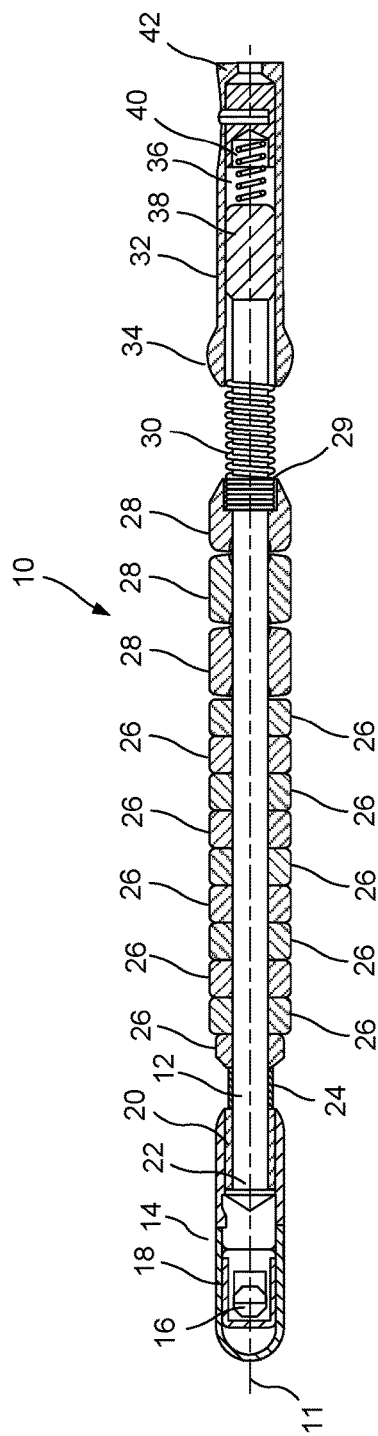
FIG. 1 is a cross-sectional view an embodiment of the source wire assembly of the present disclosure.

Referring now to the figures in detail, wherein like numerals indicate like elements throughout the several views, one sees that FIG. 1 is a cross-sectional view of an embodiment of the source wire assembly 10 of the present disclosure.

Source wire assembly 10 is substantially rotationally symmetric about longitudinal axis 11 and is intended for radiographic uses such as, but not limited to, a radiographic projector which includes a curved or serpentine path. The curved or serpentine path of the radiographic projector is typically bounded by heavy radiological shielding. The curved or serpentine path, in combination with the heavy radiological shielding, provides for substantially reduced radiation emitted through the path to the exterior, particularly if there is no line of sight from the exterior of the radiological projector to the radiological source of the source wire assembly 10. The total shielding is further increased, and the emitted radiation to the exterior of the radiographic projector is decreased, by the various metallic or otherwise shielding elements comprising the source wire assembly 10.

Figure 2:
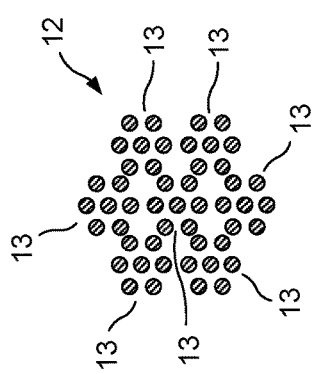
FIG. 2 is a cross-sectional view of a non-exclusive example of flexible cable which may be used for the core of the source wire assembly of FIG. 1.

Source wire assembly 10 includes an interior cylindrical core 12 of flexible metal cable. An exemplary, but non-limiting, embodiment of the flexible metal cable is shown in FIG. 2, wherein aircraft-type cable is presented with seven strands 13, each of the strands including seven metallic wires, resulting in what is commonly known as 7×7 aircraft cable. The wires are twisted, helix wound, woven, or braided together within each strand and the strands are likewise twisted, helix wound, woven or braided together to form the resulting cable. However, as will be appreciated by those skilled in the art after review of this disclosure, other configurations of aircraft cable or flexible metallic cable may be substituted for 7×7 aircraft cable. The various components of the source wire assembly 10 are mounted, directly or indirectly, on the cylindrical core 12. This allows the source wire assembly 10 to operate with freedom of movement in multiple planes and degrees of motion.

Radioactive source capsule assembly 14 includes a radioactive gamma ray source 16 encased within a housing 18. The housing 18 includes a blind aperture 20 for receiving, surrounding and securing the distal end 22 of the cylindrical core 12. It is intended that a wide range of prior art or standard radioactive source capsule assemblies 14 may be adaptable to this embodiment. Typically, the source capsule assembly 14 is permanently attached to the cylindrical core 12. The source capsule assembly 14 being attached at the end of cylindrical core 12 allows for axial radiographic applications of the radiographic projector (not shown).

A cylindrical spacer sleeve 24, typically metallic, coaxially surrounds a portion of the cylindrical core and is used to space the radioactive source assembly 14 from the shield beads 26 and maintain the proper axial alignment of the various components. The shield beads 26 are metallic toroidal rings with a central passageway through which the cylindrical core 12 passes. The shield beads 26 provide radiological shielding from the source capsule assembly 14. The cylindrical spacer sleeve 24 further assures that all gaps are filled between the shield beads 26, thereby eliminating or reducing any catch points. The cylindrical spacer sleeve 24 further aids in the permanent attachment process by preventing shield beads 26 from falling into the swaging assembly and further allows the active source capsule assembly 14 to be cut off when the assembly is returned for disposal.

Shield beads 26, which are made from a gamma shielding material, such as, but not limited to, tungsten, are illustrated in FIG. 1 as a series of ten individual toroidal rings abutting each other, with a hollow passageway through which cylindrical core 12 passes. Those skilled in the art, after review of the present disclosure, will recognize that a range of equivalent shielding materials may be used, depending upon the application. Shield beads 26 radiologically shield the proximal end of the source wire assembly 10, as well as any attached equipment such as the rear port of a radiographic projector (not shown), from the radioactive source 16. Shield beads 26 may further include beveled outer circular edges to aid in the flexure of the source wire assembly 10. The leftmost or most distal shield bead 26 is of a reduced diameter and has a more pronounced chamfered face. The purpose of this profile is to gradually transfer from the larger diameter of the shield beads 26 to the smaller diameter of the sleeve 24. This helps to prevent or minimize "hang-up" incidents or accidents from occurring. However, the remaining shield beads 26 have a diameter for a tight tolerance within the passageway of the radiographic projector in order to provide sufficient radiological shielding.

Spacer beads 28 and coil spring 30 sequentially engage the interior cylindrical core 12. The spacer beads 28 are typically made from a metal, such as, but not limited to, stainless steel. Those skilled in the art, after review of the present disclosure, will recognize that a range of equivalent materials may be used, depending upon the application. A first end of coil spring 30 may be engaged within undercut cylindrical slot 29 of rightmost spacer bead 28, radially outwardly adjacent from cylindrical core 12, in order to prevent coil spring 30 from riding over the chamfered surface of the rightmost spacer bead 28 and likewise eliminates or reduces any snagging of the first end of coil spring 30 during operation of the source wire assembly 10 (commonly known as a "hang-up incident" or "hang-up accident"). The capturing of the interior cylindrical core 12 of flexible metal cable by cylindrical spacer sleeve 24, coil spring 30 and beads 26, 28 eliminates or reduces the risk of "bird caging", or inelastic curved deformation, during repeated use. Furthermore, the chamfered faces on the shield beads 26 and spacer beads 28 allow for minimal bend radii of the overall source wire assembly 10.

Coil spring 30 further engages against connector housing 32 whereby a second end of coil spring 30 enters a cylindrical slot 33 formed by an indented relationship between sleeve 35 (swaged onto cylindrical core 12) and connector housing 32. This configuration is intended to eliminate or reduce any snagging of the second end of coil spring 30 during operation of the source wire assembly 10 (commonly known as a "hang-up incident" or "hang-up accident"). Connector housing 32 includes an enlarged distal lip 34 to further provide a diameter similar to or greater than that of shield beads 26 and spacer beads 28. This ensures that the source assembly adequately activates the source locking mechanism inside the radiographic projector (not shown) during operation. Cylindrical core 12 is engaged within the hollow interior 36 of connector housing 32 so that the proximal end of the cable 12 is surrounded by the enlarged distal lip 34 and sleeve 35. Hollow interior 36 further houses cylindrical connector shield 38, which may be made from tungsten, which provides further shielding to any attached equipment such as the rear port of a radiographic projector (not shown), from the radioactive source 16. Connector shield 38 may be biased in position by internal coil spring 40. Connector housing 32 further provides a standard connection device 42 for attachment to driving equipment, such as, but not limited to, a push-pull operation associated with a radiographic projector, which may include source wire locking and safety mechanisms.

Figure 3:
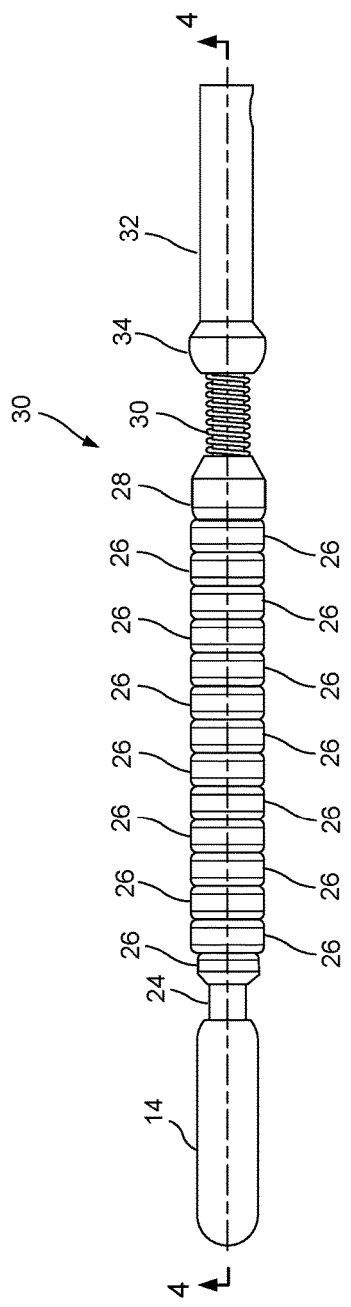
FIG. 3 is a side plan view of an alternative embodiment of the source wire assembly of the present disclosure.
Figure 4:
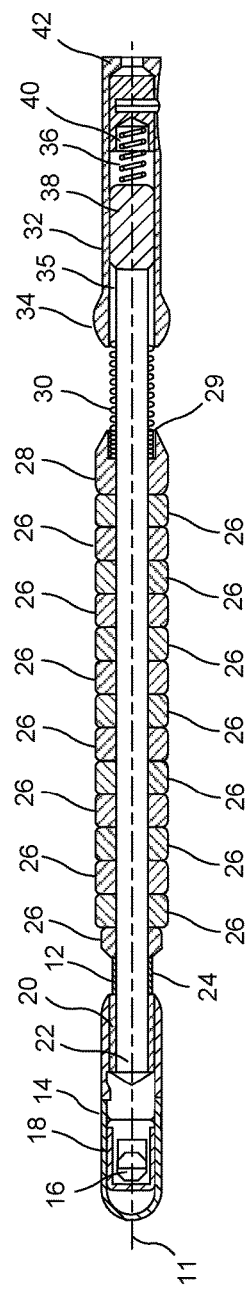
FIG. 4 is a cross-sectional view along plane 4-4 of FIG. 3, illustrating an alternative embodiment of the source wire assembly of the present disclosure.

In the alternative embodiment of the source wire assembly 10 of FIGS. 3 and 4, the two spacer beads 28 after the rightmost spacer bead 28 have been replaced by four additional shield beads 26 (with a single spacer bead 28 remaining in the rightmost position). This alternative embodiment of the source wire assembly 10 is expected to provide for increased shielding efficiency in the associated radiography projector (not shown) by reducing the radioactive dose emanating from the rear port of the projector (not shown) when the source wire assembly 10 is in the locked secure position. This results in increased safety to the operator or handler of the device and further provides a safety factor to avoid potential non-conforming shield efficiency profiles when the projector and the source wire assembly 10 enter the production stage of manufacture.

Thus the several aforementioned objects and advantages are most effectively attained. Although preferred embodiments of the invention have been disclosed and described in detail herein, it should be understood that this invention is in no sense limited thereby.

What is claimed is:

1. A source wire assembly for radiographic applications, including traversing a curved path of a radiographic projector, including:
   an axial core comprising a cable including a plurality of metallic strands, the axial core including a distal end and a proximal end;
   the distal end including a device for holding a radiographic source and the proximal end including a device for connecting to a drive apparatus; and
   a plurality of toroidal rings mounted on the cable, wherein a first portion of the toroidal rings are metallic shielding beads, and a second portion of the toroidal rings is at least one stainless steel spacer bead positioned to a proximal side of the metallic shielding beads.

2. The source wire assembly of claim 1 wherein the plurality of metallic strands are intertwined with each other.

3. The source wire assembly of claim 2 wherein each of the strands include a plurality of metal wires.

4. The source wire assembly of claim 3 wherein the plurality of metal wires within each strand are intertwined with each other.

5. The source wire assembly of claim 4 wherein the strands are intertwined in a configuration chosen from the group consisting of twisted, helix wound, woven and braided.

6. The source wire assembly of claim 5 wherein the metal wires are intertwined in a configuration chosen from the group consisting of twisted, helix wound, woven and braided.

7. The source wire assembly of claim 1 wherein the metallic shielding beads are comprised of tungsten.

8. The source wire assembly of claim 1 further including a coil spring wrapped around the core and engaging, on a first end, a stainless steel spacer bead and, on a second end, a housing of the device for connecting to a drive apparatus.

9. The source wire assembly of claim 8 wherein the housing further includes an enlarged lip with a diameter equal to or greater than that of the plurality of toroidal rings.

10. The source wire assembly of claim 9 wherein the stainless steel spacer bead engaged by the first end of the coil spring includes an undercut cylindrical slot radially outward from the core for receiving the first end of the coil spring.

11. The source wire assembly of claim 10 wherein the second end of the spring urges against the enlarged lip of the housing.

12. The source wire assembly of claim 11 wherein the enlarged lip of the housing surrounds a proximal end of the cable.

13. The source wire assembly of claim 12 wherein the device for holding a radiological source includes a blind aperture for engaging and securing a distal end of the cable.

14. The source wire assembly of claim 8 further including a spacer sleeve coaxially surrounding a portion of the cable, the spacer sleeve including a first end and a second end, the first end of the spacer sleeve abutting the device for holding a radiographic source and the second end of the spacer sleeve abutting a most distal metallic shielding bead.

15. The wire source assembly of claim 14 wherein the most distal metallic shielding bead has a lesser diameter than a diameter of other shielding beads.

16. The source wire assembly of claim 8 wherein the device for holding a radiological source further includes a capsule assembly for encasing a radiological source.

* * * * *